United States Patent [19]

Chinuki et al.

[11] Patent Number: 5,476,652
[45] Date of Patent: Dec. 19, 1995

[54] SLOW-RELEASING MEDICATED RESIN MOLDINGS, AND PROCESS FOR PRODUCING THE SAME

[75] Inventors: Takashi Chinuki, Ibaraki; Tatsuhiro Nagamatsu, Takatsuki; Tomomi Satoh, Ibaraki, all of Japan

[73] Assignee: Sumitomo Chemical Company, Limited, Osaka, Japan

[21] Appl. No.: 83,511

[22] Filed: Jun. 30, 1993

[30] Foreign Application Priority Data

Jul. 6, 1992 [JP] Japan .................................. 4-178139
Jan. 20, 1993 [JP] Japan .................................. 5-007463

[51] Int. Cl.⁶ .......................... A01N 25/18; A01N 25/34; B29C 55/00; A61L 9/04
[52] U.S. Cl. ...................... 424/78.01; 424/409; 424/484; 424/486; 424/487; 514/263
[58] Field of Search ................... 424/78.01, 83, 424/486, 484, 487; 521/61, 62, 64; 514/263

[56] References Cited

U.S. PATENT DOCUMENTS 4,445,641  5/1984  Baker et al. .............................. 239/6
4,793,959  12/1988  Nogiwa et al. .......................... 264/41
4,959,208  9/1990  Chakrabarti et al. .................... 424/78

FOREIGN PATENT DOCUMENTS 1104926A   7/1981  Canada .
0253667A2  1/1988  European Pat. Off. .
0380353A2  8/1990  European Pat. Off. .
58-011145  1/1983  Japan .
59-59734   4/1984  Japan .
61-227031  10/1986 Japan .
62-149736  7/1987  Japan .
2080687    2/1982  United Kingdom .

Primary Examiner—Nathan M. Nutter
Attorney, Agent, or Firm—Stevens, Davis, Miller & Mosher

[57] ABSTRACT

Disclosed in this invention are the slow-releasing medicated resin moldings which are the porous bodies obtained by stretching 1.1-10 times the resin compositions comprising 100 parts by weight of a thermoplastic resin, 50 to 400 parts by weight of a filler and a drug(s) in an amount not less than the saturation dissolution rate for the thermoplastic resin, and a process for producing such slow-releasing medicated resin moldings.

11 Claims, 3 Drawing Sheets

SLOW-RELEASING MEDICATED RESIN MOLDINGS, AND PROCESS FOR PRODUCING THE SAME

BACKGROUND OF THE INVENTION

This invention relates to the medicated resin moldings which can gradually or slowly release the drug incorporated therein (hereinafter referred to as slow-releasing medicated resin moldings) and a process for producing such medicated resin moldings. More particularly, the invention relates to said slow-releasing medicated resin moldings characterized in particular by their capability of retaining a large quantity of drug and releasing the drug gradually at a constant rate, and a process for producing such slow-releasing medicated resin moldings.

A technique has been known for effecting gradual or slow release of a drug from a molding comprising a medicated resin composition prepared by uniformly incorporating a drug in a plastic resin by kneading. According to this technique, however, since the drug is released out to the ambience from the surface of the resin molding with the lapse of time and the drug release rate lowers as the drug content in the resin molding decreases, it was difficult to maintain release of the drug at a constant rate. Also, the maximal amount of a drug compatible with resin, although variable depending on the type of resin and drug used, is usually as low as about 0.1 to 5% by weight in the case of thermoplastic resins, so that constant release of the drug over a prolonged period of time could not be expected of the conventional medicated resin moldings. Even if a drug was blended in a large amount, such as exceeding the saturation dissolution rate, in the resin composition, it was still unable to realize long-time constant release of a drug because, in such a case, there would occur bleeding of the drug or mass release of the drug in the early time of use.

The present inventors have pursued studies in search of a drug slow-releasing technique which makes it possible for a molding to contain a large amount of drug without causing bleeding and also enables release of a drug at a constant rate over a prolonged period of time. As a result, the inventors found that a slow-releasing medicated resin molding capable of retaining a drug at a high content and releasing it at a constant rate can be obtained by making a medicated porous body from a resin composition comprising a resin, a filler and a drug in an amount exceeding the saturation dissolution rate for said resin by means of mono- or biaxial stretching. The present invention was achieved on the basis of this finding.

Thus, in accordance with the present invention, there are provided:

1. A slow-releasing medicated resin molding, wherein a drug is contained in a porous resin molding obtained by stretching 1.1–10 times a resin composition comprising 100 parts by weight of a thermoplastic resin and 50 to 400 parts by weight of a filler, the amount of the drug is not less than the saturation dissolution rate for the thermoplastic resin.

2. A process for producing a slow-releasing medicated resin molding, which comprises stretching 1.1– 10 times mono- or biaxially a resin composition comprising 100 parts by weight of a thermoplastic resin, 50 to 400 parts by weight of a filler and a drug in an amount not less than the saturation dissolution rate for the thermoplastic resin, whereby the composition is made porous.

3. A process for producing a slow-releasing medicated resin molding, which comprises stretching 1.1– 10 times mono- or biaxially a resin composition comprising 100 parts by weight of a thermoplastic resin and 50 to 400 parts by weight of a filler, wherein stretching is conducted in a state where said resin composition is immersed in or applied with a drug or its solution to make the composition porous.

4. A process for producing a slow-releasing medicated resin molding, which comprises impregnating the porous resin molding obtained by stretching 1.1–10 times mono- or biaxially a resin composition comprising 100 parts by weight of a thermoplastic resin and 50 to 400 parts by weight of a filler with a drug in an amount not less than the saturation dissolution rate for the thermoplastic resin.

5. A vermin control method using a slow-releasing medicated resin molding which is a porous body obtained by stretching 1.1–10 times a resin composition comprising 100 parts by weight of a thermoplastic resin and 50 to 400 parts by weight of a filler, and adding thereto at least one insecticide selected from the group consisting of pyrethroids, methoxydiazone and pyriproxyfen in an amount not less than the saturation dissolution rate for the thermoplastic resin.

DETAILED DESCRIPTION OF THE INVENTION

The thermoplastic resins usable in the present invention include polyolefin resins, for example, α-olefin homopolymers such as low-density polyethylenes, high-density polyethylenes, polypropylene and polybutene, copolymers of ethylene and at least one α-olefin selected from α-olefins having 3 to 18 carbon atoms and copolymers of propylene, ethylene and/or butene-1; copolymers of ethylene, vinyl acetate and/or organic carboxylic acid derivatives having ethylenic unsaturated bonds such as acrylic acid esters and methacrylic acid esters, and the like. These resins may be used either singly or in combination. Of these resins, copolymer of ethylene and at least one α-olefin selected from α-olefins having 3–8 carbon atoms is especially preferred in view of strength when the filler is blended. Use of a thermoplastic resin of which 20% by weight or more is constituted by a linear low-density polyethylene which is a copolymer of ethylene and an α-olefin selected from α-olefins having 4–8 carbon atoms and which has a density of 0,870–0.915 g/cm$^3$, is even more favorable for the reason of good stretchability of the composition at a low temperature.

In the composition of the present invention, the filler content is usually 50 to 400 parts by weight for 100 parts by weight of the thermoplastic resin. When the filler content is less than 50 parts by weight, the total volume of microvoids in the resin molding which has been made porous by stretching is insufficient, while when the filler content exceeds 400 parts by weight, workability of the composition is deteriorated. In view of working stability, the preferred range of filler content is 70 to 200 parts by weight.

Examples of the fillers usable in the present invention include carbonates such as calcium carbonate, magnesium carbonate and barium carbonate, sulfates such as barium sulfate, magnesium sulfate and calcium sulfate, phosphates such as magnesium phosphate and calcium phosphate, hydroxides such as magnesium hydroxide and aluminum hydroxide, oxides such as alumina, silica, magnesium oxide, calcium oxide, zinc oxide and titanium oxide, chlorides such as zinc chloride, iron chloride and sodium chloride, active carbon inorganic fillers such as aluminum powder, zeolite, shirasu, clay, diatomaceous earth, talc, carbon black and volcanic ash, cellulose powders such as woodmeal and pulp powder, synthetic resin powders such as nylon powder, polycarbonate powder, polypropylene powder and poly-4-methyl-pentene- 1 powder, and organic fillers such as xanthone powder, chitin powder and starch. These fillers may be used singly or in combination.

In view of flexibility and appearance of the molding, calcium carbonate is especially preferred for use as a filler.

The filler used in the present invention is preferably the one having an average particle size of 1 to 100 μm since the filler in this range of particle size has excellent dispersibility and contributes to effecting the constant release rate of a drug from the medicated resin molding.

The drug content in the molding of this invention is not less than the saturation dissolution rate for the thermoplastic resin. However, the drug content is not more than about 350 parts by weight per 100 parts by weight of the thermoplastic resin because excessive content causes bleedout of the drug. The porous slow-releasing medicated resin molding of this invention is a body having a multitude of microvoids formed by stretching. These microvoids are not closed and form through-holes with each other, and the drug stays therein, so that the drug in an amount not less than the saturation dissolution rate for the thermoplastic resin exist in the resin molding, there is no possibility of causing bleedout of the drug to the surface. The "saturation dissolution rate for the thermoplastic resin" means the maximum amount of the drug that the resin can absorb when it is immersed in the drug. For the convenience' sake, the value shown in the present invention is the one measured at 23° C. That is, in case the drug is solid at 23° C., the resin and drug are mixed in the state of being melted by heating, and when the mixture is cooled to 23° C. and left as it is, the maximaum amount of the drug that can be uniformly dispersed in the resin without causing crystallization in the inside and surface of the resin is the amount at the "saturation dissolution rate" referred to herein.

The drug used in the molding of this invention is not specified. The drug used here means an active ingredient or its formulation. At least one of the drugs selected from commercially available insecticides, antifungal agents, repellents, germicides, rust inhibitors and aromatics, however, can be used. The following can be cited as typical examples of the drugs usable in the molding of this invention. The insecticides include pyrethroid type insecticides such as Permethrin, allethrin, d-allethrin, dd,allethrin, pralethrin, cyphenothrin, d-phenothrin, d-resmethrin, empenthrin, fenvalerate, fenpropathrin, cyhalothrin, cyfluthrin, ethofenprox, tralomethrin, benfluthrin, teralethrin and phenothrin; organophosphorous insecticides such as fenitrothion, dichlorvos, naled, fenthion, ciaphos, chlorpyrifos, Diazinon and calclofos; insecticidal compounds such as methoxydiazone; carbamate type insecticides such as Propoxur, fenobucarb and carbaril; and insect growth regulating substances such as pyriproxyphen, methoprene, hydroprene, diflubenzurone, cyromazine, lubenuron (CGA 184 694) and fenoxycarb. As the compounds that help elevate the effect of these insecticides, there are known piperonyl butoxide, MGK 264 (N-(2-ethylhexyl)-8,9,10-trinorborn-5-ene-2,3-dicarboximide), octachlorodipropyl ether, etc. These compounds can be used in combination with said insecticides.

The vermin repellents usable in this invention include diethyltoluamide, dibutyl phthalate and the like. The antifungal agents include dehydroacetic acid, 4-isopropyl-m-cresol, n-butyl benzyl phthalate and allyl isothiocyanate. The germicides include cresol, resorcin and the like. The vegetable essential oils also usable in the composition of this invention include hinoki essential oil, hiba essential oil, getto essential oil, mustard extract oil, wasabi (Wasabi japonica matsum) extract oil and the like. Some of these vegetable essential oils have the germicidal and antifungal activities as well as the aromatic activity, so that they can be used not only as an aromatic but also as a germicidal or antifungal agent in certain uses.

A typical process for obtaining a slow-releasing medicated resin molding according to the present invention is described below.

First, 100 parts by weight of thermoplastic resin, 50 to 400 parts by weight of a filler and a drug in an amount not less than the saturation dissolution rate for the thermoplastic resin, if necessary plus pertinent additives such as dispersant, stabilizer, etc., are mixed and/or kneaded in a usual way, for example, by using a roll or Banbury type mixer or a single- or double-screw extruder to obtain a resin composition. Then this composition is molded into sheets usually from 30 μm to 10 mm in thickness, strands or rods usually from 30 μm to 10 mm in diameter and the composition in the form of a sheet, rod or strand is monoaxially or biaxially stretched 1.1 to 10 times at a temperature usually in the range of 10° to 140° C., preferably 20° to 140° C., to obtain the desired slow-releasing medicated resin moldings in such a form as sheet, film, rod or strand.

The preferred stretching temperature differs depending on the resin composition, but when the stretching temperature is below 10° C., stability of the composition when stretched is bad, while use of a temperature exceeding 140° C. for stretching discourages formation of microvoids in the molding.

As for the stretching method, roll stretching or stretching by a draw die is employed in the case of monoaxial stretching. In the case of biaxial stretching, it is possible to perform stretching in both directions simultaneously (simultaneous biaxial stretching) or to first perform stretching in the machine direction and then conduct stretching in the transverse direction (successive biaxial stretching).

The stretch ratio is usually within the range of 1.1 to 10 times. When the stretch ratio is less than 1.1 time, the porosity (ratio of the total volume of microvoids per unit weight of the resin molding) is so low that the drug which has bled out from the resin is unable to stay stably in the resin molding. On the other hand, when the stretch ratio exceeds 10 times, there may result undesirable phenomena such as breaking of resin or excessive enlargement of the size of microvoids.

The thus obtained moldings can be used without any further treatment. If necessary, however, the moldings are annealed to prevent them from shrinking. The annealing temperature is preferably between the stretching temperature and the melting point of the resin.

The porosity of the resin molding is variable depending on a stretching temperature, stretch ratio, filler concentration and the kind of thermoplastic resin. The porosity of the resin molding just after stretching is usually 0.1 cc/g or higher.

In case the drug is liquid, it may be used in the form as it is or after diluted with a volatile or non-volatile solvent for the preparation of the resin composition before stretching. In case the drug is solid, it may be mixed as is with the resin and filler, followed by stretching of the mixture, or the drug may be used after dissolved in a volatile or non-volatile solvent.

In case the drug can not be beforehand mixed with the resin and filler for some reason or other (for example, because of the possibility that the drug might be volatilized away or decomposed in heating), initially 100 parts by weight of the thermoplastic resin and 50 to 400 parts by weight of the filler, if necessary plus pertinent additives such as dispersant, stabilizer, etc., are mixed or kneaded by an ordinary method using a roll type or Banbury type mixer or kneader or a single- or double-screw extruder to obtain a composition, and this composition is molded into sheets of usually from 30 μm to 10 mm in thickness, strands or rods usually from 30 μm to 10 mm in diameter, and stretched 1.1 to 10 times at a temperature usually in the range of 10 to 140° C., preferably 20° to 140° C., in a state of being immersed in or applied with the drug or a solution prepared by dissolving the drug in a volatile solvent, thus obtaining a medicated resin molding. According to this process, since the drug is incorporated in the microvoids formed by stretching, there can be obtained the desired slow-releasing medicated resin moldings.

The moldings of the present invention can also be produced as follows. A resin composition comprising 100 parts by weight of a thermoplastic resin and 50 to 400 parts by weight of a filler is stretched 1.0 to 10 times to obtain a porous resin molding, and the molding is impregnated with a drug or its solution. Alternatively, the drug or its solution may be applied to the molding. The medicated resin moldings thus obtained also contain drugs in an amount not less than the saturation dissolution rate for the thermoplastic resin.

For controlling the drug release rate in more preferred range, an additional resin composition may be laminated on the surface of the medicated resin molding of the present invention. An additional thermoplastic resin composition layer is provided on a partial surface area or an entire surface area of a resin composition sheet comprising 100 parts by weight of thermoplastic resin, 50 to 400 parts by weight of filler and a drug in an amount not less than the saturation dissolution rate for the thermoplastic resin. These laminated resin composition layers are then mono- or biaxially stretched 1.1 to 10 times to obtain a slow-releasing medicated resin laminate. It is also possible to obtain a slow-releasing medicated resin laminate by applying, as by laminating, a thermoplastic resin composition layer on a partial surface area or an entire surface area of the medicated resin molding of this invention.

When the moldings are in the form of a strand or rod, a resin composition comprising 100 parts by weight of a thermoplastic resin and 50 to 400 parts by weight of a filler, and a drug in an amount not less than the saturation dissolvution rate for the thermoplastic resin provided with thermoplastic resin composition layer on a partial surface area or an entire surface area are stretched 1.1 to 10 times.

Moreover, the medicated porous moldings in the form of a strand or rod may be immersed in a solution of a thermoplastic resin in a solvent, then the moldings are pulled up, and the solvent is evaporated to provide the thermoplastic resin on a partial surface area or an entire surface area of the medicated resin moldings.

The thermoplastic resin composition layer thus provided on the medicated resin molding does not completely hinder a drug from permeating therethrough but has a permeability to it. The rate of the permeation can be controlled by choosing the kind or thickness of the layer or the kind of the filler.

The thermoplastic resins that can be additionally applied for forming said laminate in this invention include α-olefin homopolymers such as low-density polyethylenes, high-density polyethylenes, polypropylene and polybutene, copolymer of ethylene and at least one α-olefin selected from α-olefins having 3 to 18 carbon atoms, copolymer of propylene, ethylene and/or butene-1, and the like. These thermoplastic resins may be used singly or as a mixture.

It is possible to use mixtures of these thermoplastic resins with inorganic fillers which include carbonates such as calcium carbonate, magnesium carbonate and barium carbonate, sulfates such as barium sulfate, magnesium sulfate and calcium sulfate, phosphates such as magnesium phosphate and calcium phosphate, hydroxides such as magnesium hydroxide and aluminum hydroxide, oxides such as alumina, silica, magnesium oxide, calcium oxide, zinc oxide and titanium oxide, chlorides such as zinc chloride, iron chloride and sodium chloride, aluminum powder, zeolite, shirasu, clay, diatomaceous earth, talc, carbon black, volcanic ash, etc., or organic fillers which include cellulose powders such as woodmeal and pulp powder, synthetic resin powders such as nylon powder, polycarbonate powder, polypropylene powder and poly-4-methylpentene-1 powder, starch, active carbon, xanthone powder, chitin powder and the like.

In case the drug used in the present invention has a certain degree of vapor pressure (e.g., $1 \times 10^{-5}$ to $1 \times 10^{-2}$ mmHg), the drug is released by volatilization from the surface of the resin portion of the molding and that of microvoids exposed in the surface. In the resin portion, the drug exists in an amount equivalent to the saturation dissolution rate for the resin in the initial stage, so that when release of the drug begins, a concentration gradient is produced between the releasing surface and the inside of the resin molding. Since the drug exists plentifully in the microvoids, there takes place transfer of the drug from the microvoids into the resin portion until an equilibrium is reached. Since this state of equilibrium is maintained until the drug in the microvoids runs out, the releasing rate of the drug is kept constant throughought the releasing period.

In case the vapor pressure is fairly low (e.g., less than $1 \times 10^{-5}$ mmHg), release of the drug by volatilization from the surface of the resin molding is slight, but when the drug in the resin or on the surfaces of microvoids is lost, with resultant decrease of surface layer concentration, as a result of direct adsorption of the drug from the resin or microvoid surfaces through contact with them or indirect adsorption through a medium, there takes place transfer of the drug from the microvoids as in the above-described case, so that the surface layer concentration is maintained constant, and consequently the gradual release rate of the drug is substantially kept constant.

The slow-releasing medicated resin molding according to this invention is capable of retaining a drug in an amount not less than the saturation dissolution rate for the thermoplastic resin and releasing the drug at a constant rate, so that it is very useful as a medicated resin molding that slowly releases the drug contained therein such as an insecticide, an antifungal agent, a germicide, an aromatic, a rust inhibitor or the like. Thus, the resin molding of this invention can be used for insect controlling, prevention of growth of mold, sterilization, or as an aromatic by properly selecting the drug incorporated in the resin molding.

The present invention will hereinafter be described more particularly by showing the examples thereof, which examples however are merely intended to be illustrative and not to be construed as limiting the scope of the invention in any way. The methods for determination of product properties and the methods of efficacy evaluation tests used in the following examples and comparative examples are as described below.

① Saturation dissolution rate:

A 50×50×0.5 mm sheet molded from a thermoplastic resin was immersed in a liquid drug at 23° C., and the ratio of the amount of the drug absorbed in the sheet at the point when absorption of resin has reached saturation after a given period of time to the amount of the resin at that time was expressed as saturation dissolution rate (of the drug).

② Drug release rate

Figure 2:
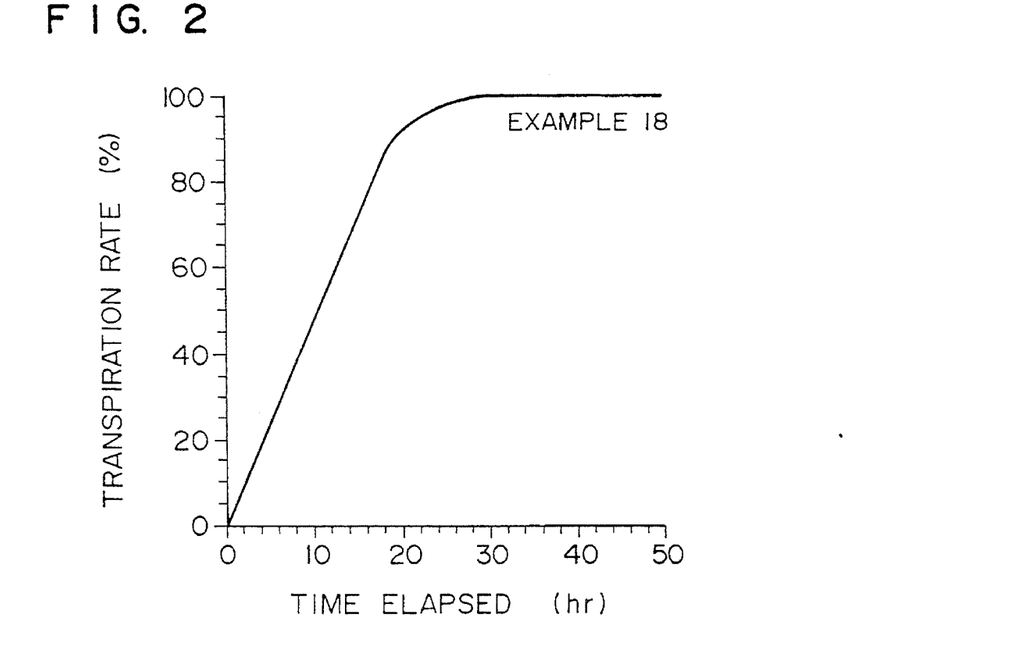
FIG. 2 is a graph showing the change of transpiration rate with time of the drug of Example 18 (Table 4).
Figure 3:
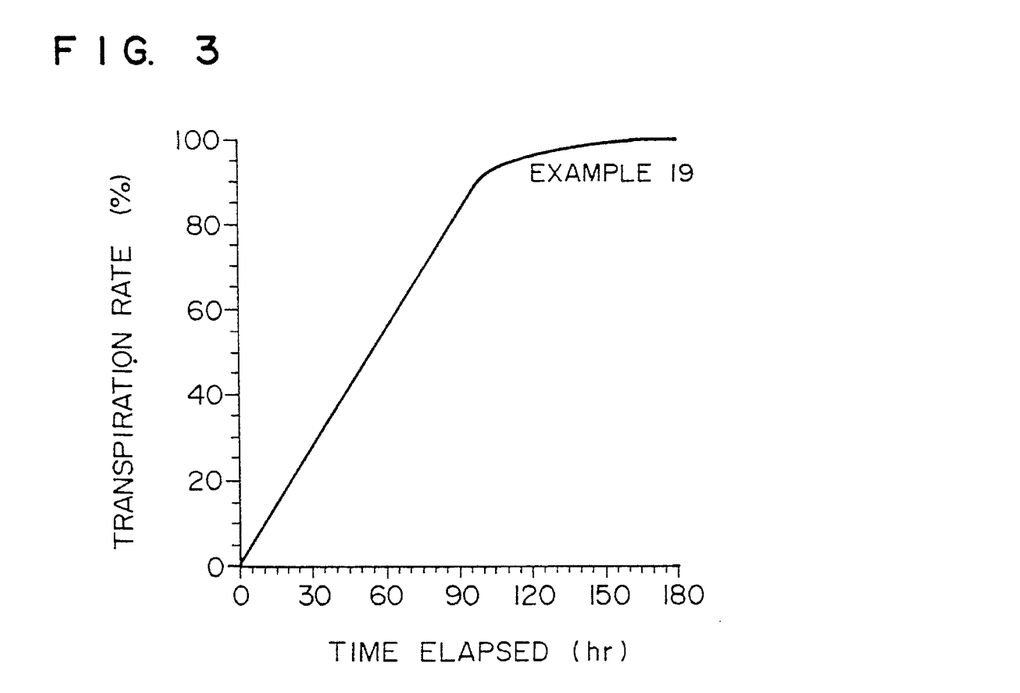
FIG. 3 is a graph showing the change of transpiration rate with time of the drug of Example 19 (Table 4).
Figure 4:
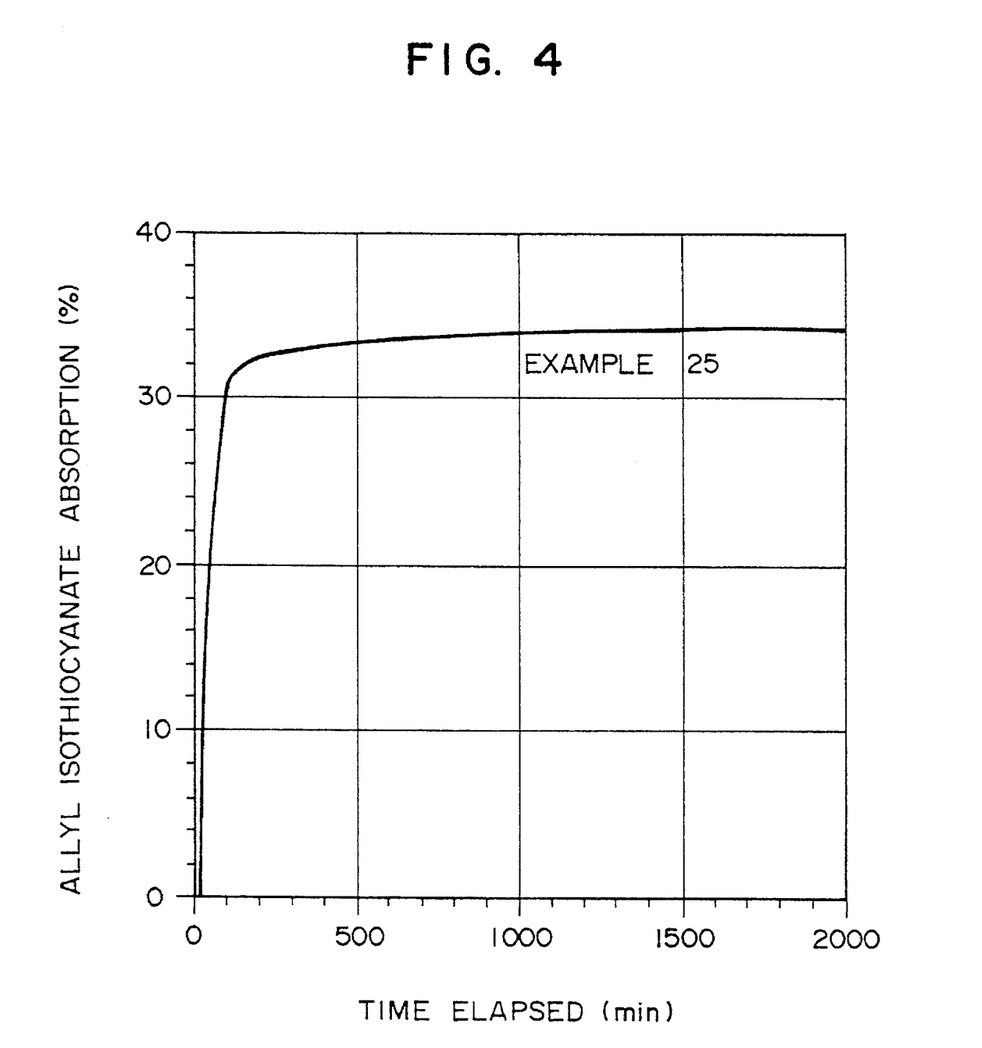
FIG. 4 is a graph showing the change of allyl isothiocyanate absorption with time of the drug of Example 25.

The drug release rate from the medicated resin molding was determined in the following way. The medicated resin molding was cut into 4 cm×10 cm test pieces (releasing area: 80 cm$^2$) and suspended in a 40° C. thermostatic chamber, and the weight loss of the drug in the molding was examined from the change of weight and the transpiration rate of the drug from each of the test pieces was determined from the following equation and shown in Tables 3 and 4 and FIGS. 1–3.

Transpiration rate= (amount of drug released after a given period of time)÷ (initial amount of drug)×100

③ Bleedout:

Bleedout of the drug to the surface of the medicated resin molding was visually observed and evaluated.

④ Efficacy evaluation tests a) Evaluation of initial efficacy

Test insects

Blattella germanica (adults, sex ratio= 1)
Coptotermers formosanus (worker)
Ctenocephalides felis Testing method The groups of each species of test insects (each group comprising 10 insects) were released on each of the test resins, and the number of the knocked down insects was counted periodically over a period of 120 minutes to determine KT50 (time required for knocking down 50% of the test insects). The number of the dead insects was counted 3 days after start of the test for the cockroaches, one day after start of the test for the termites and one day after start of the test for the fleas to determine the lethal ratio (%). Each test was conducted thrice repeatedly. The results are shown in Table 3.

The sizes of the resins used for the tests were as follows:

15×15 cm for cockroaches
7.5×7.5 cm for termites
7.5×7.5 cm for fleas b) Evaluation of efficacy persistency Testing method The surface of each test resin was wiped with ethanol-impregnated gauze to clean away the drug from the resin surface, the resin was left under room temperature for one day to have ethanol perfectly evaporated away while stabilizing the drug concentration on the resin surface, after which the same test as in the case of initial efficacy evaluation was conducted. The results are shown in Table 4.

EXAMPLE 1

100 parts by weight of a linear low-density polyethylene (excellenVL VL200, produced by Sumitomo Chemical Co., Ltd.) as thermoplastic resin, 120 parts by weight of calcium carbonate (whiton SSB (red), produced by Shiraishi Calcium K.K.) as filler, and 55 parts by weight of empenthrin (vaporthrin, Sumitomo Chemical Co., Ltd.) as a drug were mixed by a Banbury mixer at 120° C. for 5 minutes to form a resin composition. This resin composition was T-die extruded into a 1 mm thick sheet, and this sheet was stretched 4 times monoaxially (in the machine direction) at 50° C. by a roll stretcher to obtain a slow-releasing medicated resin molding.

The thus obtained slow-releasing medicated resin molding had good workability, was free of bleedout of the drug to the surface and showed high potency.

EXAMPLE 2

A slow-releasing medicated resin molding was obtained by following the same procedure as Example 1 except for use of phenothrin (sumithrin, Sumitomo Chemical Co., Ltd.) as the drug. This slow-releasing medicated resin molding had good workability, was also free of bleedout of the drug to the surface and showed high potency.

EXAMPLE 3

A slow-releasing medicated resin molding was obtained by following the same procedure as Example 1 except that 20 parts by weight of a linear low-density polyethylene excellenVL VL200, Sumitomo Chemical Co., Ltd.), 60 parts by weight of another linear low-density polyethylene (Sumikathene-α CS3003, Sumitomo Chemical Co., Ltd.) and 20 parts by weight of a low-density polyethylene (Sumikathene F208-0, Sumitomo Chemical Co., Ltd.) were used as thermoplastic resin. The obtained slow-releasing medicated resin molding had good workability, was free of bleedout of the drug to the surface and showed high potency.

EXAMPLE 4

100 parts by weight of a linear low-density polyethyalene (excellenVL VL200, Sumitomo Chemical Co., Ltd.) as thermoplastic resin and 120 parts by weight of calcium carbonate (whiton SSB (red), Shiraishi Calcium K.K.) as filler were mixed by a Banbury mixer at 120° C. for 5 minutes to obtain a resin composition. This resin composition was T-die extruded into a 1 mm thick sheet and this sheet was stretched 4 times monoaxially at 50° C. by a roll stretcher in a state where the sheet was immersed in an empenthrin solution to obtain a slow-releasing medicated resin molding.

The drug adhering to the sheet surface was cleared away and the content of empenthrin in the obtained resin molding was determined to be 45 parts by weight.

This slow-releasing medicated resin molding had good workability, was free of bleedout of the drug to the surface and showed high potency.

EXAMPLE 5

On both sides of the porous body obtained in Example 1, a low-density polyethylene (Sumikathene G801, Sumitomo Chemical Co., Ltd.) was laminated to a thickness of 50 μm to obtain a slow-releasing medicated resin laminate.

This slow-releasing medicated resin laminate was free of bleedout of the drug to the surface and showed high potency.

EXAMPLE 6

On both sides of the porous body obtained in Example 1, a linear low-density polyethylene (excellenVL VL200, Sumitomo Chemical Co., Ltd.) was laminated to a thickness of 50 μm to obtain a slow-releasing medicated resin laminate.

This slow-releasing medicated resin laminate was free of bleedout of the drug to the surface and showed high potency.

EXAMPLE 7

A slow-releasing medicated resin molding was obtained by following the same procedure as Example 1 except that roll stretching was performed at room temperature (23° C.).

The obtained slow-releasing medicated resin molding had good workability, was free of bleedout of the drug to the surface and showed high potency.

EXAMPLE 8

A slow-releasing medicated resin molding was obtained by following the same procedure as Example 1 except that the amount of the filler blended was changed to 150 parts by weight and the amount of the drug to 135 parts by weight, and that roll stretching was conducted at room temperature (23° C.).

The obtained slow-releasing medicated resin molding had good workability, was free of bleedout of the drug to the surface and showed high potency.

EXAMPLE 9

A slow-releasing medicated resin molding was obtained in the same way as Example 1 except that 40 parts by weight of a linear low-density polyethylene (excellenVL VL200, Sumitomo Chemical Co., Ltd.) and 60 parts by weight of another linear low-density polyethylene (Sumikathene-α FZ201-0, Sumitomo Chemical Co., Ltd.) were used as thermoplastic resin, that 150 parts by weight of calcium carbonate (whiton SSB (red), Shiraishi Calcium K.K.) was used as filler, that 135 parts by weight of hinoki essential oil (produced by Kishu Hinokiya Co., Ltd.) was used as drug, and that roll stretching was carried out at room temperature (23° C.).

The obtained slow-releasing resin molding had good workability, was free of bleedout of the drug to the surface and showed high potency.

EXAMPLE 10

A slow-releasing medicated resin molding was obtained in the same way as Example 4 except that the amount of the filler blended was 150 parts by weight, that allyl isothiocyanate (wasaouro, The Green Cross Corporation) was used as drug, and that roll stretching was performed at room temperature (23° C.). The content of allyl isothiocyanate in 100 parts by weight of the resin molding was 65 parts by weight.

The obtained slow-releasing medicated resin molding was free of bleedout of the drug to the surface and showed high potency.

EXAMPLE 11

A slow-releasing medicated resin molding was obtained in the same way as Example 1 except that 3 parts by weight of pyriproxyfen (Sumilarv, Sumitomo Chemical Co., Ltd.) and 40 parts by weight of d-allethrin (pynamin forte, Sumitomo Chemical Co., Ltd.) were used as drug. This slow-releasing medicated resin molding had good workability, was free of bleedout of the drug to the surface and showed high potency.

EXAMPLE 12

A slow-releasing medicated resin molding was obtained in the same way as Example 1 except that 3 parts by weight of pyriproxyfen Sumilarv, Sumitomo Chemical Co., Ltd.) and 40 parts by weight of methoxydiazone (Elemic, Sumitomo Chemical Co., Ltd.) were blended as drug. The obtained slow-releasing medicated resin molding had good workability, was free of bleedout of the drug to the surface and showed high potency.

EXAMPLE 13

A slow-releasing medicated resin molding was obtained in the same way as Example 1 except that 100 parts by weight of a linear low-density polyethylene (Sumikathene-α FZ201-0, Sumitomo Chemical Co., Ltd.) was used as thermoplastic resin, that 150 parts by weight of calcium carbonate (whiton SSB (red), Shiraishi Calcium K.K.) was used as filler, that 3 parts by weight of pyriproxyfen, 36 parts by weight of phenothrin and 72 parts by weight of N-(2-ethylhexyl)-8,9,10-trinorbon-5-ene- 2,3-dicarboximide were used as drug, and that roll stretching was conducted at room temperature (23 ° C.). The obtained slow-releasing medicated resin molding had good workability, was free of bleedout of the drug to the surface and showed high potency.

COMPARATIVE EXAMPLE 1

100 parts by weight of a linear low-density polyethylene (excellenVL VL200, Sumitomo Chemical Co., Ltd.) as thermoplastic resin, 40 parts by weight of calcium carbonate (whiton SSB (red), Shiraishi Calcium K.K.) as filler and 55 parts by weight of empenthrin (vaporthrin, Sumitomo Chemical Co., Ltd.) as drug were mixed at 120° C. for 5 minutes by a Banbury mixer to form a resin composition.

This resin composition was T-die extruded into a 1 mm thick sheet and this sheet was stretched 4 times monoaxially at 50° C. by a roll stretcher to obtain a slow-releasing medicated resin molding.

This resin molding caused bleedout of empenthrin from the inside due to low porosity and could not be offered to practical use.

COMPARATIVE EXAMPLE 2

A resin composition was obtained by mixing 100 parts by weight of a linear low-density polyethylene (excellenVL VL200, Sumitomo Chemical Co., Ltd.) as thermoplastic resin, 450 parts by weight of calcium carbonate (whiton SSB (red), Shiraishi Calcium K.K.) as filler and 55 parts by weight of empenthrin (vaporthrin, Sumitomo Chemical Co., Ltd.) as agent at 12° C. for 5 minutes by a Banbury mixer.

This resin composition was T-die extruded into a 1 mm thick sheet, and it was tried to stretch the sheet 4 times monoaxially at 50° C. by a roll stretcher. But the sheet ruptured and it was unable to obtain a desired slow-releasing medicated resin molding.

COMPARATIVE EXAMPLE 3

A resin composition was obtained and a 1 mm thick sheet was formed therefrom in the same way as Example 1 except that no stretching was conducted. The obtained sheet caused bleedout of empenthrin from the inside as it was not porous, and this sheet could not be offered to practical use.

COMPARATIVE EXAMPLE 4

A resin composition was obtained by mixing 100 parts by weight of a linear low-density polyethylene (excellenVL VL200, Sumitomo Chemical Co., Ltd.) as thermoplastic resin, 120 parts by weight of calcium carbonate (whiton SSB (red), Shiraishi Calcium K.K.) as filler and 55 parts by weight of empenthrin (vaporthrin, Sumitomo Chemical Co., Ltd.) as drug at 120° C. for 5 minutes by a Banbury mixer. This resin composition was T-die extruded into a 1 mm thick sheet, and it was tried to stretch this sheet 12 times monoaxially at 50° C. by a roll stretcher. But the sheet ruptured and it was unable to obtain a desired slow-releasing medicated resin molding.

EXAMPLE 14

100 parts by weight of a linear low-density polyethylene (excellenVL VL200, Sumitomo Chemical Co., Ltd., saturation dissolution rate of empenthrin: 2.3 wt %) as thermoplastic resin, 120 parts by weight of calcium carbonate (whiton SSB (red), Shiraishi Calcium K.K.) as filler and 40 parts by weight of empenthrin (vaporthrin, Sumitomo Chemical Co., Ltd., vapor pressure at 20° C.: $6.5 \times 10^{-4}$ mmHg) as drug were mixed by a Banbury mixer at 120° C. for 5 minutes to obtain a resin composition.

This resin composition was T-die extruded into a 1 mm thick sheet and this sheet was stretched 4 times monoaxially at 50° C. by a roll stretcher to obtain a slow-releasing medicated resin molding.

The release rate of the drug from the obtained resin molding was measured. As shown in Table 3 and FIG. 1, the drug release rate per unit time was controlled to remain constant, and this resin molding was confirmed to be a very efficacious slow-releasing medicated molding.

EXAMPLE 15

On the sides of the porous body obtained in Example 14, a low-density polyethylene (Sumikathene G801, Sumitomo Chemical Co., Ltd.) was laminated to a thickness of 50 μm to obtain a slow-releasing medicated resin molding. This medicated resin molding showed high potency as shown in Table 3 and FIG. 1.

EXAMPLE 16

On both sides of the porous body obtained in Example 14, a linear low-density polyethylene (excellenVL VL200, Sumitomo Chemical Co., Ltd.) was laminated to a thickness of 50 μm to obtain a slow-releasing medicated resin molding. This medicated resin molding showed high potency as shown in Table 3 and FIG. 1.

EXAMPLE 17

On both sides of the porous body obtained in Example 14, a high-density polyethylene (Sholex 5050, Showa Denko K.K.) was laminated to a thickness of 80 μm to obtain a slow-releasing medicated resin molding. This medicated resin molding showed high potency as shown in Table 3 and FIG. 1.

EXAMPLE 18

A resin composition was obtained by mixing 100 parts by weight of a linear low-density polyethylene (excellenVL VL200, Sumitomo Chemical Co., Ltd., saturation dissolution rate of allyl isothiocyanate: 4.5 wt %) as thermoplastic resin and 150 parts by weight of calcium carbonate (whiton SSB (red), Shiraishi Calcium K.K.) as filler by a Banbury mixer at 120° C. for 5 minutes. This resin composition was T-die extruded into a 1 mm thick sheet and this sheet was stretched 4 times monoaxially at room temperature (23° C.) by a roll stretcher in a state where the sheet was immersed in a solution of allyl isothiocyanate (wasaouro, The Green Cross Corporation, vapor pressure at 20° C.: 4 mmHg) to obtain a slow-releasing medicated resin molding.

On both sides of this resin molding, a low-density polyethylene (Sumikathene F208-0, Sumitomo Chemical Co., Ltd.) was laminated to a thickness of 50 μm to obtain a slow-releasing medicated resin molding. This product showed high potency as shown in Table 4 and FIG. 2.

EXAMPLE 19

A slow-releasing medicated resin molding was obtained in the same way as Example 18 except that a high-density polyethylene (Sholex 5050, Showa Denko K.K.) was laminated on both sides of the resin molding. The obtained slow-releasing medicated resin molding showed high potency as shown in Table 4 and FIG. 3.

COMPARATIVE EXAMPLE 5

A resin composition was obtained by mixing 100 parts by weight of a linear low-density polyethylene (excellenVL VL200, Sumitomo Chemical Co., Ltd.) as thermoplastic resin, 40 parts by weight of calcium carbonate (whiton SSB (red), Shiraishi Calcium K.K.) as filler and 40 parts by weight of empenthrin (vaporthrin, Sumitomo Chemical Co., Ltd.) as drug by a Banbury mixer at 120° C. for 5 minutes. This resin composition was T-die extruded into a 1 mm thick sheet and this sheet was stretched 4 times monoaxially at 50° C. by a roll stretcher to obtain a slow-releasing medicated resin molding.

Bleedout of empenthrin took place from the inside of the obtained medicated resin molding due to its low porosity, and this medicated resin molding was unsuited for practical use.

COMPARATIVE EXAMPLE 6

A resin composition was obtained by mixing 100 parts by weight of a linear low-density polyethylene (excellenVL VL200, Sumitomo Chemical Co., Ltd.) as thermoplastic resin, 450 parts by weight of calcium carbonate (whiton SSB (red), Shiraishi Calcium K.K.) as filler and 40 parts by weight of empenthrin (vaporthrin, Sumitomo Chemical Co., Ltd.) as drug by a Banbury mixer at 120° C. for 5 minutes.

This resin composition was T-die extruded into a 1 mm thick sheet and it was tried to stretch this sheet 4 times monoaxially at 50° C. by a roll stretcher. But the sheet ruptured and it was unable to obtain a desired slow-releasing medicated resin molding.

COMPARATIVE EXAMPLE 7

A resin composition was obtained and a sheet was made therefrom in the same way as Example 14 except that no stretching was conducted. The obtained sheet suffered bleedout of empenthrin from the inside as it was non-porous, and it could not be applied to practical use.

COMPARATIVE EXAMPLE 8

A resin composition was obtained by mixing 100 parts by weight of a linear low-density polyethylene (excellenVL VL200, Sumitomo Chemical Co., Ltd.) as thermoplastic resin, 120 parts by weight of calcium carbonate (whiton SSB (red), Shiraishi Calcium K.K.) as filler and 40 parts by weight of empenthrin (vaporthrin, Sumitomo Chemical Co., Ltd.) as drug by a Banbury mixer at 120° C. for 5 minutes.

This resin composition was T-die extruded into a 1 mm thick sheet and it was tried to stretch this sheet 12 times monoaxially at 50° C. by a roll stretcher. But the sheet ruptured and it was unable to obtain a desired slow-releasing medicated resin molding.

COMPARATIVE EXAMPLE 9

A slow-releasing medicated resin molding was obtained in the same way as Example 14 except that the content of the drug was reduced to 2 parts by weight.

Figure 1:
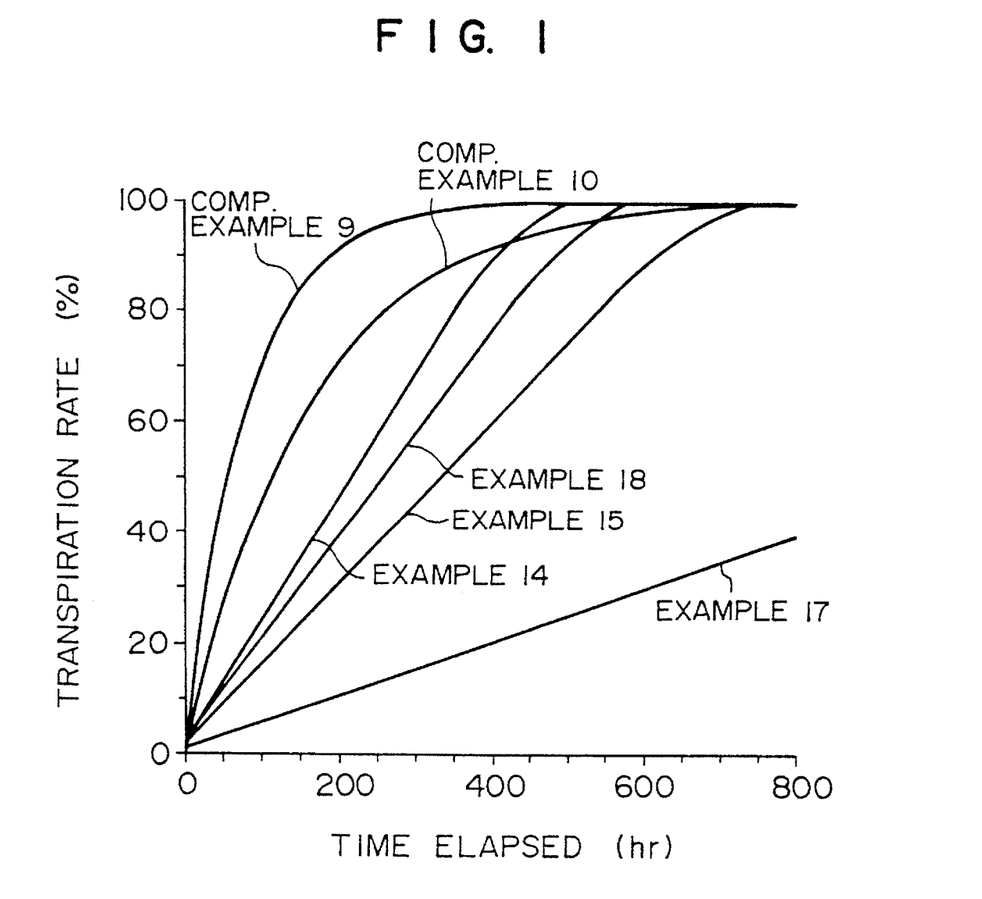
FIG. 1 is a graph showing the change of transpiration rate with time of the drugs of Examples 14–17 and Comparative Examples 9 and 10 (Table 3).

Measurement of the release rate of the drug from the obtained medicated resin molding showed that the release rate per unit time decreased with time as shown in Table 3 and FIG. 1.

COMPARATIVE EXAMPLE 10

A resin composition was obtained by mixing 100 parts by weight of an ethylene-methyl methacrylate copolymer (Acryft WH202, Sumitomo Chemical Co., Ltd., saturation dissolution rate of empenthrin: 14 wt %) as thermoplastic resin and 15 parts by weight of empenthrin as drug by a Banbury mixer at 120° C. for 5 minutes.

This resin composition was T-die extruded into a 1 mm thick sheet and a slow-releasing medicated resin molding was obtained therefrom.

Measurement of the release rate of the drug from the obtained medicated resin molding showed that the release rate per unit time decreased with time as shown in Table 3 and FIG. 1.

EXAMPLE 20

A resin composition was obtained by mixing 100 parts by weight of a linear low-density polyethylene (excellenVL VL200, Sumitomo Chemical Co., Ltd., saturation dissolution rate of phenothrin: 2.2 wt %) as thermoplastic resin, 120 parts by weight of calcium carbonate (whiton SSB (red), Shiraishi Calcium K.K.) as filler and 22 parts by weight of phenothrin (sumithrin, Sumitomo Chemical Co., Ltd.) as drug by a Banbury mixer at 120° C. for 5 minutes.

This resin composition was T-die extruded into a 1 mm thick sheet and this sheet was stretched 4 times monoaxially at 50° C. by a roll stretcher to obtain a slow-releasing medicated resin molding.

The obtained slow-releasing medicated resin molding was free of bleedout of the drug to the surface, and as shown in Tables 5 and 6, it had very high initial effect of knockdown and killing of insects and retention of efficacy. The product was suited for slow release of a contact type drug.

EXAMPLE 21

On both sides of the porous body obtained in Example 20, a low-density polyethylene (Sumikathene G801, Sumitomo Chemical Co., Ltd.) as thermoplastic resin was laminated to a thickness of 50 μm to obtain a slow-releasing medicated resin molding. This slow-releasing medicated resin molding was free of bleedout of the drug to the surface, and as shown in Tables 5 and 6, it had very high initial effect of knockdown and killing of insects and retention of effect. This embodiment was excellent for slow release of a drug.

EXAMPLE 22

On both side is of the porous body obtained in Example 20, a linear low-density polyethylene (excellenVL VL200, Sumitomo Chemical Co., Ltd.) as thermoplastic resin was laminated to a thickness of 50 μm to obtain a slow-releasing medicated resin molding. This medicated resin molding was free of bleedout of the drug to the surface, and as shown in Tables 5 and 6, it had very high initial effect of knockdown and killing of insects and retention of effect. It is noted that this embodiment is excellent for slow release of a drug.

EXAMPLE 23

On both sides of the porous body obtained in Example 20, a high-density polyethylene (Sholex 5050, Showa Denko K.K.) as thermoplastic resin was laminated to a thickness of 80 μm to obtain a slow-releasing medicated resin molding. This medicated resin molding was free of bleedout of the drug to the surface, and as shown in Tables 5 and 6, it had very high initial effect of knockdown and killing of noxious insects and retention of effect. This embodiment was found to be excellent for slow release of a drug.

EXAMPLE 24

A resin composition was obtained by mixing 100 parts by weight of a linear low-density polyethylene (excellenVL VL200, Simitomo Chemical Co., Ltd.) as thermoplastic resin, 120 parts by weight of calcium carbonate (whiton SSB (red), Shiraishi Calcium K.K.) as filler and 55 parts by weight of empenthrin (vaporthrin, Sumitomo Chemical Co., Ltd.) as drug by a Banburg mixer at 120° C. for 5 minutes.

This resin composition was extruded into a 1 mm diameter strand. This strand was stretched 4 times monoaxially (MD) at 23° C. by a draw die 600 μm in bore diameter to obtain a slow-releasing medicated resin molding.

The obtained slow-releasing medicated resin molding had good workability, was free of fleedout of the drug to the surface and showed high potency.

EXAMPLE 25

A resin composition was obtained by mixing 100 parts by weight of a linear low-density polyethylene (excellenVL VL200) as thermoplastic resin and calcium carbonate (callite SA, Shiraishi Calcium K.K.) as filler by a Banbury mixer at 120° C. for 5 minutes.

This resin composition was T-die extruded into a 1.6 mm thick sheet and this sheet was stretched 4 times monoaxially at 23° C. by a roll stretcher to obtain a porous sheet.

The obtained porous sheet was impregnated with a solution of allyl isothiocyanate (wasaouro, The Green Cross Corporation) and allyl isothiocyanate absorption was measured with the lapse of time. After 30 minutes from starting the impregnation, the absorption became constant. And then the sheet was pulled up and allyl isothiocyanate on the surface of the sheet was wiped out to obtain a slow-releasing medicated resin molding.

COMPARATIVE EXAMPLE 11

A resin composition was obtained by mixing 100 parts by weight of a linear low-density polyethylene (excellenVL VL200, Sumitomo Chemical Co., Ltd.) as thermoplastic resin, 40 parts by weight of calcium carbonate (whiton SSB (red), Shiraishi Calcium K.K.) as filler and 40 parts by weight of phenothrin (sumithrin, Sumitomo Chemical Co., Ltd.) as drug by a Banbury mixer at 120° C. for 5 minutes.

This resin composition was T-die extruded into a 1 mm thick sheet and this sheet was stretched 4 times monoaxially at 50° C. by a roll stretcher to obtain a slow-releasing medicated resin molding.

The obtained medicated resin molding was subject to bleedout of the drug from the inside due to low porosity and could not be applied to practical use.

COMPARATIVE EXAMPLE 12

A resin composition was obtained by mixing 100 parts by weight of a linear low-density polyethylene (excellenVL VL200, Sumitomo Chemical Co., Ltd.) as thermoplastic resin, 450 parts by weight of calcium carbonate (whiton SSB (red), Shiraishi Calcium K.K.) as filler and 40 parts by weight of phenothrin (sumithrin, Sumitomo Chemical Co., Ltd.) as drug by a Banbury mixer at 120° C. for 5 minutes.

This resin composition was T-die extruded into a 1 mm thick sheet and it was tried to stretch this sheet 4 times monoaxially at 50° C. by a roll stretcher. But the sheet ruptured and it was unable to obtain a desired slow-releasing medicated resin molding.

COMPARATIVE EXAMPLE 13

A resin composition was obtained and a 1 mm thick sheet was made therefrom in the same way as Example 20 except that no stretching was conducted. The obtained sheet suffered bleedout of phenothrin from the inside as it was non-porous, and it was unsuited for practical use.

COMPARATIVE EXAMPLE 14

A resin composition was obtained by mixing 100 parts by weight of a linear low-density polyethylene (excellenVL VL200, Sumitomo Chemical Co., Ltd.) as thermoplastic resin, 120 parts by weight of calcium carbonate (whiton SSB (red), Shiraishi Calcium K.K.) as filler and 40 parts by weight of phenothrin (sumithrin, Sumitomo Chemical Co., Ltd.) as drug by a Banbury mixer at 120° C. for 5 minutes.

This resin composition was T-die extruded into a 1 mm thick sheet, and it was tried to stretch this sheet 12 times monoaxially at 50° C. by a roll stretcher. The sheet ruptured in the course of stretching, and it was unable to obtain a desired slow-releasing medicated resin molding.

COMPARATIVE EXAMPLE 15

A slow-releasing medicated resin molding was obtained in the same way as Example 20 except that the content of the drug was reduced to 2 parts by weight. The obtained product was free of bleedout of the drug to the surface but very low in knockdown and killing effects against insects as shown in Tables 5 and 6.

COMPARATIVE EXAMPLE 16

A resin composition was obtained by mixing 100 parts by weight of an ethylene-methyl methacrylate copolymer (Acryft WH202, Sumitomo Chemical Co., Ltd., saturation dissolution rate of phenothrin: 15 wt %) as thermoplastic resin and 15 parts by weight of phenothrin as drug by a Banbury mixer at 120° C. for 5 minutes.

This resin composition was T-die extruded into a 1 mm thick sheet and this sheet was worked as in the proceeding examples to obtain a slow-releasing medicated resin molding. The obtained product was free of bleedout of the drug to the surface but very low in knockdown and killing effects against insects as shown in Tables 5 and 6.

COMPARATIVE EXAMPLE 17

A resin composition was obtained by mixing 100 parts by weight of vinyl chloride (Sumilit Sx-13F, Sumitomo Chemical Co., Ltd.) as thermoplastic resin, 43 parts by weight of DOA as plasticizer and 25 parts by weight of phenothrin as drug by roll milling for 5 minutes.

This resin composition was T-die extruded into a 1 mm thick sheet. The obtained product was free of bleedout of the drug to the surface and high in initial efficacy as shown in Table 5 but very low in retention of efficacy as shown in Table 6.

TABLE 1

| | Resin/ Parts by weight | Parts by weight of filler | Drug/ Parts by weight | Layers on both/ Thickness |
|---|---|---|---|---|
| Example 1 | A/100 | 120 | a/55 | |
| Example 2 | A/100 | 120 | b/55 | |
| Example 3 | A/20 B/60 C/20 | 120 | a/55 | |
| Example 4 | A/100 | 120 | a/45 | |
| Example 5 | A/100 | 120 | a/55 | D/50 μm |
| Example 6 | A/100 | 120 | a/55 | A/50 μm |
| Example 7 | A/100 | 120 | a/55 | |
| Example 8 | A/100 | 150 | a/135 | |
| Example 9 | A/40 E/60 | 150 | c/135 | |
| Example 10 | A/100 | 150 | d/65 | |
| Example 11 | A/100 | 120 | e/3 f/40 | |
| Example 12 | A/100 | 120 | e/3 g/40 | |
| Example 13 | E/100 | 150 | b/36 e/3 h/72 | |
| Example 14 | A/100 | 120 | a/40 | |
| Example 15 | A/100 | 120 | a/40 | D/50 μm |
| Example 16 | A/100 | 120 | a/40 | A/50 μm |
| Example 17 | A/100 | 120 | a/40 | G/80 μm |
| Example 18 | A/100 | 150 | d | C/50 μm |
| Example 19 | A/100 | 150 | d | G/50 μm |
| Example 20 | A/100 | 120 | b/22 | |
| Example 21 | A/100 | 120 | b/22 | D/50 μm |
| Example 22 | A/100 | 120 | b/22 | A/50 μm |
| Example 23 | A/100 | 120 | b/100 | G/80 μm |
| Example 24 | A/100 | 120 | a/55 | |
| Example 25 | A/100 | 100 | d | |
| Comp. Example 1 | A/100 | 40 | a/55 | |
| Comp. Example 2 | A/100 | 450 | a/55 | |
| Comp. Example 3 | A/100 | 120 | a/55 | |
| Comp. Example 4 | A/100 | 120 | a/55 | |

TABLE 1-continued

|  | Resin/ Parts by weight | Parts by weight of filler | Drug/ Parts by weight | Layers on both/ Thickness |
|---|---|---|---|---|
| Comp. Example 5 | A/100 | 40 | a/40 | |
| Comp. Example 6 | A/100 | 450 | a/40 | |
| Comp. Example 7 | A/100 | 120 | a/40 | |
| Comp. Example 8 | A/100 | 120 | a/40 | |
| Comp. Example 9 | A/100 | 120 | a/2 | |
| Comp. Example 10 | F/100 | — | a/15 | |
| Comp. Example 11 | A/100 | 40 | b/40 | |
| Comp. Example 12 | A/100 | 450 | b/40 | |
| Comp. Example 13 | A/100 | 120 | b/22 | |
| Comp. Example 14 | A/100 | 120 | b/40 | |
| Comp. Example 15 | A/100 | 120 | b/2 | |
| Comp. Example 16 | F/100 | — | b/15 | |
| Comp. Example 17 | H/100 | — | b/25 | |

Resin A: linear low-density polyethylene (excellenVL VL200, Sumitomo Chemical Co., Ltd., comonomer: butene-1, density: 0.900 g/cm³)
Resin B: linear low-density polyethylene (Sumikathene-α CS3003, Sumitomo Chemical Co., Ltd., comonomer: hexane-1, density: 0.933 g/cm³)
Resin C: low-density polyethylene (Sumikathene F208-0, Sumitomo Chemical Co., Ltd., density: 0.922 g/cm³)
Resin D: low-density polyethylene (Sumikathene G801, Sumitomo Chemical Co., Ltd.)
Resin E: linear low-density polyethylene (Sumikathene-α FZ201-0, Sumitomo Chemical Co., Ltd., comonomer: hexane-1, density: 0.912 g/cm³)
Resin F: ethylene-methyl methacrylate copolymer (Acryft WH202, Sumitomo Chemical Co., Ltd.)
Resin G: high-density polyethylene (Sholex 5050, Showa Denko K.K.)
Resin H: vinyl chloride (Sumilit Sx-13F, Sumitomo Chemical Co., Ltd.)
Filler: calcium carbonate (whiton SSB (red), Shiraishi Calcium K.K.), in Example 25 calcium carbonate (Callite SA, Shiraishi Calcium K.K.)
Agent a: empenthrin (vaporthrin, Sumitomo Chemical Co., Ltd.)
Agent b: phenothrin (sumithrin, Sumitomo Chemical Co., Ltd.)
Agent c: hinoki essential oil (Kishu Hinokiya)
Agent d: allyl isothiocyanate (wasaouro, The Green Cross Corporation)
Agent e: pyriproxyfen (Sumilarv, Sumitomo Chemical Co., Ltd.)
Agent f: d-allethrin (pynamin forte, Sumitomo Chemical Co., Ltd.)
Agent g: methoxydiazone (Elemic, Sumitomo Chemical Co., Ltd.)
Agent h: N-(2-ethylhexyl)-8,9,10-trinorborn-5-ene-2,3-dicarboximide (MGK 264)

Evaluation of workability and bleedout

The sheets were stretched 4 times in the air at 50° C. in Examples 1–3, 5, 6, 14–17 and 20–23, in a drug at 50° C. in Example 4 and in the air at 23° C. in Examples 7–13, 18, 19, 24 and 25. All the sheets showed good workability, and the obtained products were free of bleedout.

TABLE 2

| Run No. | Stretching environment/ Temperature | Stretch ratio | Workability | Bleedout |
|---|---|---|---|---|
| Comp. Example 1 | In the air/50° C. | 4 | — | Observed |
| Comp. Example 2 | In the air/50° C. | 4 | Ruptured while stretched | — |
| Comp. Example 3 | Non-stretched | — | — | Observed |
| Comp. Example 4 | In the air/50° C. | 12 | Ruptured while stretched | — |
| Comp. Example 5 | In the air/50° C. | 4 | — | Observed |
| Comp. Example 6 | In the air/50° C. | 4 | Ruptured while stretched | — |
| Comp. Example 7 | Non-stretched | — | — | Observed |
| Comp. Example 8 | In the air/50° C. | 12 | Ruptured while stretched | — |
| Comp. Example 9 | In the air/50° C. | 4 | — | — |
| Comp. Example 10 | Non-stretched | — | — | — |
| Comp. Example 11 | In the air/50° C. | 4 | — | Observed |
| Comp. Example 12 | In the air/50° C. | 4 | Ruptured while stretched | — |
| Comp. Example 13 | Non-stretched | — | — | Observed |
| Comp. Example 14 | In the air/50° C. | 12 | Ruptured while stretched | — |
| Comp. Example 15 | In the air/50° C. | 4 | — | — |
| Comp. Example 16 | Non-stretched | — | — | — |
| Comp. Example 17 | Non-stretched | — | — | — |

TABLE 3

Transpiration rate of drug from the medicated resin moldings

| Time elapsed (hr) | 0 | 7 | 20 | 43 | 68 | 118 | 165 | 210 |
|---|---|---|---|---|---|---|---|---|
| Example 14 | 0 | 5.2 | 7.3 | 12.1 | 17.0 | 28.9 | 39.4 | 49.5 |
| Example 15 | 0 | 2.5 | 5.6 | 9.4 | 12.7 | 20.2 | 26.5 | 33.2 |
| Example 16 | 0 | 3.5 | 7.0 | 11.3 | 16.7 | 25.6 | 33.7 | 43.5 |
| Example 17 | 0 | 1.1 | 1.7 | 2.9 | 4.1 | 6.7 | 8.7 | 10.8 |
| Comp. Example 9 | 0 | 10.0 | 21.5 | 39.2 | 54.3 | 77.5 | 87.5 | 95.0 |
| Comp. Example 10 | 0 | 3.5 | 11.9 | 22.5 | 34.0 | 52.5 | 64.0 | 73.0 |

| Time elapsed (hr) | 253 | 370 | 455 | 530 | 576 | 605 | 698 |
|---|---|---|---|---|---|---|---|
| Example 14 | 60.2 | 84.9 | 97.9 | 100.0 | | | |
| Example 15 | 39.8 | 56.5 | 69.8 | 80.0 | 86.0 | 88.9 | 94.9 |
| Example 16 | 52.1 | 71.1 | 87.0 | 92.1 | 96.0 | 98.1 | 100.0 |
| Example 17 | 13.2 | 18.4 | 23.5 | 27.8 | 29.2 | 29.7 | 34.9 |
| Comp. Example 9 | 97.5 | 100.0 | | | | | |
| Comp. Example 10 | 80.0 | 91.1 | 94.9 | 96.0 | 97.0 | 98.1 | 98.9 |

TABLE 4

Transpiration rate of drug from the medicated resin moldings

| Time elapsed (hr) | 0 | 1 | 2.5 | 3.5 | 10 | 19 | 28 | 43 |
|---|---|---|---|---|---|---|---|---|
| Example 18 | 0 | 6.2 | 15.2 | 21.2 | 48.0 | 85.7 | 98.6 | 100 |
| Example 19 | 0 | 0.8 | 2.4 | 3.3 | 11.1 | 19.7 | 29.4 | 41.9 |

| Time elapsed (hr) | 50 | 70 | 77 | 100 | 123 | 148 | 174 |
|---|---|---|---|---|---|---|---|
| Example 18 | | | | | | | |
| Example 19 | 47.4 | 65.8 | 70.5 | 89.5 | 91.5 | 95.0 | 100 |

TABLE 5

Results of evaluation of initial efficacy

| | Blattella germanica | | Coptotermers formosanus | |
|---|---|---|---|---|
| | KT50 (min) | Fatality (%) | KT50 (min) | Fatality (%) |
| Example 20 | 30.0 | 55 | 16.9 | 100 |
| Example 21 | 40.5 | 45 | 6.7 | 100 |
| Example 22 | 16.3 | 100 | 6.6 | 100 |
| Example 23 | 19.1 | 81 | 5.8 | 100 |
| Comp. Example 15 | >120 | 0 | 58.3 | 30 |
| Comp. Example 16 | 90.6 | 20 | 74.4 | 43 |
| Comp. Example 17 | 18.8 | 88 | 7.2 | 100 |

| | Ctenocephalides felis | |
|---|---|---|
| | KT50 (min) | Lethal ratio (%) |
| Example 20 | 31.3 | 100 |
| Example 21 | 23.5 | 100 |
| Example 22 | 20.1 | 100 |
| Example 23 | 18.6 | 100 |
| Comp. Example 15 | >120 | 45 |
| Comp. Example 16 | >120 | 70 |
| Comp. Example 17 | 36.6 | 100 |

TABLE 6

Results of evaluation of retention of efficacy

| | Blattella germanica | | Coptotermers formosanus | |
|---|---|---|---|---|
| | KT50 (min) | Fatality (%) | KT50 (min) | Fatality (%) |
| Example 20 | 42.1 | 42 | 21.4 | 92 |
| Example 21 | 40.8 | 33 | 7.0 | 100 |
| Example 22 | 15.9 | 100 | 8.2 | 100 |
| Example 23 | 16.7 | 100 | 5.8 | 100 |
| Comp. Example 15 | >120 | 0 | >120 | 0 |
| Comp. Example 16 | >120 | 0 | >120 | 0 |
| Comp. Example 17 | >120 | 33 | 88.6 | 20 |

TABLE 6-continued

Results of evaluation of retention of efficacy

| | Ctenocephalides felis | |
|---|---|---|
| | KT50 (min) | Lethal ratio (%) |
| Example 20 | 42.2 | 100 |
| Example 21 | 24.8 | 100 |
| Example 22 | 16.2 | 100 |
| Example 23 | 17.5 | 100 |
| Comp. Example 15 | >120 | 11 |
| Comp. Example 16 | >120 | 5 |
| Comp. Example 17 | 110.5 | 44 |

What is claimed is:

1. A slow-releasing medicated resin molding, wherein an organic drug selected from the group consisting of insecticides, antifungal agents, repellents, germicides, rust inhibitors, aromatics and mixtures thereof is contained in a porous resin molding obtained by stretching 1.1–10 times a resin composition comprising 100 parts by weight of a thermoplastic resin selected from the group consisting of α-olefin homopolymers, copolymers of ethylene and at least One a-olefin selected from α-olefins having 3 to 18 carbon atoms copolymers of propylene, ethylene and/or butene-1, copolymers of ethylene, vinyl acetate and/or organic carboxylic acid derivatives having ethylenic unsaturated bonds and 50 to 400 parts by weight of a filler selected from the group consisting of carbonates, sulfates, phosphates, hydroxides, oxides, chlorides, inorganic fillers, cellulose powders, synthetic resin powders and organic fillers, the amount of the drug being not less than the saturation dissolution rate for the thermoplastic resin.

2. A slow-releasing medicated molding according to claim 1, wherein the molding is a sheet or a film.

3. A slow-releasing medicated resin molding according to claim 1, wherein the molding is a strand or a rod.

4. A slow-releasing medicated resin molding according to claim 1, wherein the thermoplastic resin is a polyolefin resin, the drug is one selected from the group consisting of insecticides, repellents, germicides, antifungal agents, aromatics and mixtures thereof, and the filler is calcium carbonate.

5. A slow-releasing medicated resin molding according to claim 4, wherein the drug is an insecticide selected from a group consisting of pyrethroid and mixtures thereof, methoxydiazone and pyriproxyfen.

6. A slow-releasing medicated resin molding according to claim 4, wherein the polyolefin resin is a copolymer of ethylene and at least one α-olefins having 3 to 18 carbon atoms.

7. A slow-releasing medicated resin molding according to claim 5, wherein the drug is empenthrin.

8. A slow-releasing medicated resin molding according to claim 5, the drug is phenothrin.

9. A slow-releasing medicated resin molding according to claim 4, the drug is allyl isothiocyanate.

10. The slow-releasing medicated resin molding according to claim 1 wherein the resin composition comprises a single layer.

11. A slow-releasing medicated resin molding according to claim 1, wherein the filler is at least one selected from the group consisting of calcium carbonate, magnesium carbonate, barium carbonate, calcium sulfate, magnesium sulfate, barium sulfate, calcium phosphate, magnesium phosphate, magnesium hydroxide, aluminum hydroxide, alumina, silica, magnesium oxide, calcium oxide, zinc oxide, titanium oxide, zinc chloride, iron chloride, sodium chloride, aluminum powder, zeolite, shirasu, clay, diatomaceous earth, talc, carbon black, volcanic ash, woodmeal, pulp powder, nylon powder, polycarbonate powder, polypropylene powder, poly-4-methyl-1-pentene powder, active carbon, xanthone powder, chitin powder and starch.

* * * * *